(12) United States Patent
Chang

(10) Patent No.: US 9,526,504 B2
(45) Date of Patent: Dec. 27, 2016

(54) METHOD AND APPARATUS FOR TREATING A CAROTID ARTERY

(71) Applicant: Silk Road Medical, Inc., Sunnyvale, CA (US)

(72) Inventor: David W. Chang, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 0 days.

(21) Appl. No.: 14/622,310

(22) Filed: Feb. 13, 2015

(65) Prior Publication Data
US 2015/0150562 A1 Jun. 4, 2015

Related U.S. Application Data

(63) Continuation of application No. 14/508,354, filed on Oct. 7, 2014, which is a continuation of application
(Continued)

(51) Int. Cl.
*A61M 16/00* (2006.01)
*A61M 27/00* (2006.01)
(Continued)

(52) U.S. Cl.
CPC ... *A61B 17/12109* (2013.01); *A61B 17/12036* (2013.01); *A61B 17/12045* (2013.01); *A61B 17/12136* (2013.01); *A61B 17/22* (2013.01); *A61B 17/320758* (2013.01); *A61B 17/3415* (2013.01); *A61F 2/82* (2013.01); *A61M 1/0009* (2013.01); *A61M 1/3613* (2014.02); *A61M 25/09* (2013.01); *A61M 25/104* (2013.01); *A61M 25/1011* (2013.01); *A61M 27/002* (2013.01);
(Continued)

(58) Field of Classification Search
CPC ...... A61M 16/00; A61M 16/02; A61M 27/00; A61M 39/00
See application file for complete search history.

(56) References Cited

U.S. PATENT DOCUMENTS

| 4,301,803 A | 11/1981 | Handa et al. |
| 4,771,777 A | 9/1988 | Horzewski et al. |

(Continued)

FOREIGN PATENT DOCUMENTS

| EP | 0427429 A2 | 5/1991 |
| EP | 1649829 A1 | 4/2006 |

(Continued)

OTHER PUBLICATIONS

Adami, M.D., et al., (2002) "Use of the Parodi Anti-Embolism System in Carotid Stenting: Italian Trial Results" J Endovasc Ther 9:147-154.

(Continued)

*Primary Examiner* — Tatyana Zalukaeva
*Assistant Examiner* — Ilya Treyger
(74) *Attorney, Agent, or Firm* — Fred C. Hernandez; Mintz Levin Cohn Ferris Glovksy and Popeo, P.C.

(57) ABSTRACT

One disclosed embodiment comprises a method for treating lesions in the carotid artery of a mammalian body. The method comprises transcervical access and blocking of blood flow through the common carotid artery (with or without blocking of blood flow through the external carotid artery), shunting blood from the internal carotid artery and treating the lesion in the carotid artery.

14 Claims, 5 Drawing Sheets

Related U.S. Application Data

No. 12/966,974, filed on Dec. 13, 2010, now Pat. No. 8,870,805, which is a continuation of application No. 10/996,301, filed on Nov. 22, 2004, now Pat. No. 7,998,104.

(60) Provisional application No. 60/524,069, filed on Nov. 21, 2003, provisional application No. 60/569,843, filed on May 10, 2004, provisional application No. 60/587,067, filed on Jul. 12, 2004.

(51) Int. Cl.
| | |
|---|---|
| A61B 17/12 | (2006.01) |
| A61B 17/22 | (2006.01) |
| A61B 17/3207 | (2006.01) |
| A61M 1/00 | (2006.01) |
| A61M 25/10 | (2013.01) |
| A61F 2/82 | (2013.01) |
| A61B 17/34 | (2006.01) |
| A61M 25/09 | (2006.01) |
| A61M 39/00 | (2006.01) |
| A61M 1/36 | (2006.01) |
| A61M 25/01 | (2006.01) |

(52) U.S. Cl.
CPC .......... A61B 2017/12127 (2013.01); A61B 2017/22001 (2013.01); A61B 2017/22055 (2013.01); A61B 2017/22065 (2013.01); A61B 2017/22067 (2013.01); A61B 2017/22069 (2013.01); A61B 2017/320716 (2013.01); A61M 1/3633 (2013.01); A61M 2025/0177 (2013.01); A61M 2025/1052 (2013.01); A61M 2205/7545 (2013.01)

(56) References Cited

U.S. PATENT DOCUMENTS

| | | |
|---|---|---|
| 4,840,690 A | 6/1989 | Melinyshyn et al. |
| 4,865,581 A | 9/1989 | Lundquist et al. |
| 4,921,478 A | 5/1990 | Solano et al. |
| 4,921,479 A | 5/1990 | Grayzel |
| 5,135,484 A | 8/1992 | Wright |
| 5,250,060 A | 10/1993 | Carbo et al. |
| 5,328,470 A | 7/1994 | Nabel et al. |
| 5,328,471 A | 7/1994 | Slepian |
| 5,380,284 A | 1/1995 | Don Michael |
| 5,429,605 A | 7/1995 | Bernd et al. |
| 5,769,821 A | 6/1998 | Abrahamson et al. |
| 5,782,800 A | 7/1998 | Yoon |
| 5,833,650 A | 11/1998 | Imran |
| 5,876,367 A | 3/1999 | Kaganov et al. |
| 5,895,399 A | 4/1999 | Barbut et al. |
| 5,910,154 A | 6/1999 | Tsugita et al. |
| 6,090,072 A | 7/2000 | Kratoska et al. |
| 6,146,370 A | 11/2000 | Barbut |
| 6,161,547 A | 12/2000 | Barbut |
| 6,165,199 A | 12/2000 | Barbut |
| 6,206,868 B1 | 3/2001 | Parodi |
| 6,258,115 B1 | 7/2001 | Dubrul |
| 6,270,477 B1 | 8/2001 | Bagaoisan et al. |
| 6,295,989 B1 | 10/2001 | Connors, III |
| 6,306,163 B1 | 10/2001 | Fitz |
| 6,312,444 B1 | 11/2001 | Barbut |
| 6,364,900 B1 | 4/2002 | Heuser |
| 6,383,172 B1 | 5/2002 | Barbut |
| 6,413,235 B1 | 7/2002 | Parodi |
| 6,423,032 B2 | 7/2002 | Parodi |
| 6,423,086 B1 | 7/2002 | Barbut et al. |
| 6,454,741 B1 | 9/2002 | Muni et al. |
| 6,464,664 B1 | 10/2002 | Jonkman et al. |
| 6,471,672 B1 | 10/2002 | Brown et al. |
| 6,482,172 B1 | 11/2002 | Thramann |
| 6,533,800 B1 | 3/2003 | Barbut |
| 6,540,712 B1 | 4/2003 | Parodi et al. |
| 6,551,268 B1 | 4/2003 | Kaganov et al. |
| 6,555,057 B1 | 4/2003 | Barbut et al. |
| 6,558,356 B2 | 5/2003 | Barbut |
| 6,582,396 B1 | 6/2003 | Parodi |
| 6,582,448 B1 | 6/2003 | Boyle et al. |
| 6,595,953 B1 | 7/2003 | Coppi et al. |
| 6,595,980 B1 | 7/2003 | Barbut |
| 6,605,074 B2 | 8/2003 | Zadno-Azizi et al. |
| 6,623,471 B1 | 9/2003 | Barbut |
| 6,626,886 B1 | 9/2003 | Barbut |
| 6,632,236 B2 | 10/2003 | Hogendijk |
| 6,638,245 B2 | 10/2003 | Miller et al. |
| 6,645,222 B1 | 11/2003 | Parodi et al. |
| 6,652,480 B1 | 11/2003 | Imran et al. |
| 6,663,652 B2 | 12/2003 | Daniel et al. |
| 6,669,721 B1 | 12/2003 | Bose et al. |
| 6,682,505 B2 | 1/2004 | Bates et al. |
| 6,695,861 B1 | 2/2004 | Rosenberg et al. |
| 6,702,782 B2 | 3/2004 | Miller et al. |
| 6,711,436 B1 | 3/2004 | Duhaylongsod |
| 6,736,790 B2 | 5/2004 | Barbut et al. |
| 6,755,847 B2 | 6/2004 | Eskuri |
| 6,783,511 B2 | 8/2004 | Komtebedde et al. |
| 6,830,579 B2 | 12/2004 | Barbut |
| 6,837,881 B1 | 1/2005 | Barbut |
| 6,840,949 B2 | 1/2005 | Barbut |
| 6,855,136 B2 | 2/2005 | Dorros et al. |
| 6,875,231 B2 | 4/2005 | Anduiza et al. |
| 6,878,140 B2 | 4/2005 | Barbut |
| 6,887,227 B1 | 5/2005 | Barbut |
| 6,902,540 B2 | 6/2005 | Dorros et al. |
| 6,905,490 B2 | 6/2005 | Parodi |
| 6,908,474 B2 | 6/2005 | Hogendijk et al. |
| 6,929,634 B2 | 8/2005 | Dorros et al. |
| 6,936,060 B2 | 8/2005 | Hogendijk et al. |
| 6,958,059 B2 | 10/2005 | Zadno-Azizi |
| 6,979,346 B1 | 12/2005 | Hossainy et al. |
| 7,004,924 B1 | 2/2006 | Brugger et al. |
| 7,004,931 B2 | 2/2006 | Hogendijk |
| 7,029,488 B2 | 4/2006 | Schonholz et al. |
| 7,033,344 B2 | 4/2006 | Imran |
| 7,048,758 B2 | 5/2006 | Boyle et al. |
| 7,063,714 B2 | 6/2006 | Dorros et al. |
| 7,083,594 B2 | 8/2006 | Coppi |
| 7,108,677 B2 | 9/2006 | Courtney et al. |
| 7,232,452 B2 | 6/2007 | Adams et al. |
| 7,232,453 B2 | 6/2007 | Shimon |
| 7,367,982 B2 | 5/2008 | Nash et al. |
| 7,374,560 B2 | 5/2008 | Ressemann et al. |
| 7,374,561 B2 | 5/2008 | Barbut |
| 7,422,579 B2 | 9/2008 | Wahr et al. |
| 7,458,980 B2 | 12/2008 | Barbut |
| 7,879,011 B2 | 2/2011 | Chang |
| 8,002,728 B2 | 8/2011 | Chang |
| 8,308,709 B2 | 11/2012 | Chang |
| 8,343,089 B2 | 1/2013 | Chang |
| 8,414,516 B2 | 4/2013 | Chang |
| 8,870,805 B2 | 10/2014 | Chang |
| 2001/0044598 A1 | 11/2001 | Parodi |
| 2001/0044634 A1 | 11/2001 | Don Michael et al. |
| 2001/0049517 A1 | 12/2001 | Zadno-Azizi et al. |
| 2002/0052620 A1 | 5/2002 | Barbut |
| 2002/0052640 A1 | 5/2002 | Bigus et al. |
| 2002/0068899 A1 | 6/2002 | McGuckin et al. |
| 2002/0087119 A1 | 7/2002 | Parodi |
| 2002/0128679 A1 | 9/2002 | Turovskiy et al. |
| 2002/0173815 A1 | 11/2002 | Hogendijk et al. |
| 2003/0040762 A1 | 2/2003 | Dorros et al. |
| 2003/0050600 A1 | 3/2003 | Ressemann et al. |
| 2003/0065356 A1 | 4/2003 | Tsugita et al. |
| 2003/0069468 A1 | 4/2003 | Bolling et al. |
| 2003/0186203 A1 | 10/2003 | Aboud |
| 2003/0212304 A1 | 11/2003 | Lattouf |
| 2004/0116946 A1 | 6/2004 | Goldsteen et al. |
| 2004/0127913 A1 | 7/2004 | Voss |
| 2004/0249435 A1 | 12/2004 | Andreas et al. |
| 2005/0096726 A1 | 5/2005 | Sequin et al. |

(56) References Cited

U.S. PATENT DOCUMENTS

| | | |
|---|---|---|
| 2005/0124973 A1 | 6/2005 | Dorros et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0228402 A1 | 10/2005 | Hofmann |
| 2005/0228432 A1 | 10/2005 | Hogendijk et al. |
| 2005/0267323 A1 | 12/2005 | Dorros et al. |
| 2005/0273051 A1 | 12/2005 | Coppi |
| 2006/0149350 A1 | 7/2006 | Patel et al. |
| 2006/0167437 A1 | 7/2006 | Valencia |
| 2006/0200191 A1 | 9/2006 | Zadno-Azizi |
| 2007/0198049 A1 | 8/2007 | Barbut |
| 2007/0249997 A1 | 10/2007 | Goodson et al. |
| 2008/0086164 A1 | 4/2008 | Rowe |
| 2009/0024072 A1 | 1/2009 | Criado et al. |
| 2009/0254166 A1 | 10/2009 | Chou et al. |
| 2010/0042118 A1 | 2/2010 | Garrison et al. |
| 2010/0204684 A1 | 8/2010 | Garrison et al. |
| 2010/0217276 A1 | 8/2010 | Garrison et al. |
| 2010/0228269 A1 | 9/2010 | Garrison et al. |
| 2011/0087147 A1 | 4/2011 | Garrison et al. |
| 2013/0035628 A1 | 2/2013 | Garrison et al. |
| 2013/0172852 A1 | 7/2013 | Chang |
| 2013/0197621 A1 | 8/2013 | Ryan et al. |
| 2013/0281788 A1 | 10/2013 | Garrison |
| 2014/0031682 A1 | 1/2014 | Renati et al. |
| 2014/0031925 A1 | 1/2014 | Garrison et al. |
| 2014/0046346 A1 | 2/2014 | Hentges et al. |
| 2014/0058414 A1 | 2/2014 | Garrison et al. |
| 2014/0135661 A1 | 5/2014 | Garrison et al. |
| 2014/0296769 A1 | 10/2014 | Hyde et al. |
| 2014/0296868 A1 | 10/2014 | Garrison et al. |
| 2014/0371653 A1 | 12/2014 | Criado et al. |
| 2015/0025616 A1 | 1/2015 | Chang |
| 2015/0080942 A1 | 3/2015 | Garrison et al. |

FOREIGN PATENT DOCUMENTS

| | | |
|---|---|---|
| WO | WO-95/05209 A1 | 2/1995 |
| WO | WO-98/38930 A1 | 9/1998 |
| WO | WO-99/45835 A2 | 9/1999 |
| WO | WO-99/65420 A1 | 12/1999 |
| WO | WO-00/32266 A1 | 6/2000 |
| WO | WO-00/76390 A2 | 12/2000 |
| WO | WO-02/32495 A1 | 4/2002 |
| WO | WO-03/090831 A2 | 11/2003 |
| WO | WO-2004/006803 A1 | 1/2004 |
| WO | WO-2005/051206 A1 | 6/2005 |
| WO | WO-2007/136946 A2 | 11/2007 |
| WO | WO-2009/012473 A3 | 1/2009 |
| WO | WO-2009/099764 A1 | 8/2009 |
| WO | WO-2009/100210 A1 | 8/2009 |
| WO | WO-2010/019719 A2 | 2/2010 |
| WO | PCT/US2013/054017 | 8/2013 |
| WO | PCT/US2013/069664 | 11/2013 |
| WO | PCT/US2014/031491 | 3/2014 |
| WO | PCT/US2014/032060 | 3/2014 |
| WO | PCT/US2014/042566 | 6/2014 |

OTHER PUBLICATIONS

Bates M.D., et al. "Reversal of the Direction of Internal Carotid Artery Blood Flow by Occlusion of the Common and External Carotid Arteries in a Swine Model" Catherization and Cardiovascular Intervention 60:270-275 (2003).

Bates, M.D., et al. (2004) "Internal Carotid Artery Flow Arrest/Reversal Cerebral Protection Techniques" The West Virginal Medical Journal, vol. 99:60-63.

Bergeron et al. (1999). "Percutaneous stenting of the internal carotid artery: the European Cast I Study" J. Endovasc. Surg. 6:155-159.

Bergeron P. et al. (1996) "Recurrent Carotid Disease: Will Stents be an alternative to surgery?" J Endovasc Surg; 3: 76-79.

Bettmann, M. et al, "Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association". Circulation Journal of the American Heart Association. 1998. 97:121-123. Retrieved Feb. 16, 2012.

Chang, D.W., et al, "A new approach to carotid angioplasty and stenting with transcervical occlusion and protective shunting: Why it may be a better carotid artery intervention" (J Vasc Surg 2004; 39:994-1002.).

Chang, M.D., "Carotid Angioplasty and Stenting Using Transcervical Occlusion and Protective Shunting Via a Mini Incision in the Neck: A New Technique for Difficult Femoral Access or Filter Placement May Be the Better Carotid Artery Intervention" 30th Global: Vascular and Endovascular Issues, Techniques and Horizons Symposium, New York, NY, Nov. 20-23, 2003; XXVII 6.1-XXVII 6.2.

Criado et al. (1997) "Evolving indications for and early results of carotid artery stenting" Am. J. Surg.; 174:111-114.

Criado et al. (2004). "Transcervical carotid artery angioplasty and stenting with carotid flow reversal: Surgical technique" J. Vasc. Surg. 18:257-261.

Criado et al. (2004). "Transcervical carotid stenting with internal carotid artery flow reversal: Feasibility and preliminary results" J. Vasc. Surg. 40:476-483.

Criado, F.J., et al., Access strategies for carotid artery intervention. J Invasive Cardiol, 2000. 12(1): p. 61-8.

Criado, M.D., et al. (2004) "Carotid angioplasty with internal carotid artery flow reversal is well tolerated in the awake patient" Journal of Vascular Surgery, 40(1):92-7.

Diederich et al. (2004) "First Clinical experiences with an endovascular clamping system for neuroprotection during carotid stenting" Eur. J. Vasc. Endovasc. Surg. 28:629-633.

Diethrich et al., (1996). "Percutaneous techniques for endoluminal carotid interventions" J. Endovasc. Surg. 3:182-202.

Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.

MO.MA Brochure; Proximal Flow Blockage Cerebral Protection Device—INVATEC.

Henry et al. (1999) "Carotid stenting with cerebral protection: First clinical experience using the PercuSurge GuardWire System" J. Endovasc. Surg. 6:321-331.

Momapresn (AET) 2002 Biamino, G; MO.MA as a distal protective device, University of Leipzig—Heart Center Department of Clinical and Interventional; Angiology Leipzig, Germany; 2002.

Ohki, M.D., et al., "Efficacy of a proximal occlusion catheter with reversal of flow in the prevention of embolic events during carotid artery stenting: An experimental analysis." (J Vasc Surg 2001; 33:504-9).

Ouriel, K., R. K. Greenberg, et al. (2001). "Hemodynamic conditions at the carotid blfurcation during protective common carotid occlusion," J Vasc Surg 34(4): 577-80.

Parodi et al. (2000). "Initial evaluation of carotid angioplasty and stenting with three different cerebral protection devices" J. Vasc. Surg. 32:1127-1136.

Perez-Arjona, E. A., Z. DelProsto, et al. (2004). "Direct percutaneous carotid artery stenting with distal protection: technical case report." Neurol Res 26(3): 338-41.

Reekers, J. A. (1998). "A balloon protection sheath to prevent peripheral embolization during aortoiliac endovascular procedures." Cardiovasc Intervent Radiol 21(5): 431-3.

Stecker et al., (2002). "Stent placement in common carotid and internal carotid artery stenoses with use of an open transcervical approach in a patient with previous endarterectomy" J. Vasc. Interv. Radiol. 13:413-417.

Theron, et al. "New Triple Coaxial Catheter System for Carotid Angioplasty with Cerebral Protection" . AJNR 11:869-874, Sep./Oct. 1990. 0195-6108/90/1106-0869. American Society of Neurology.

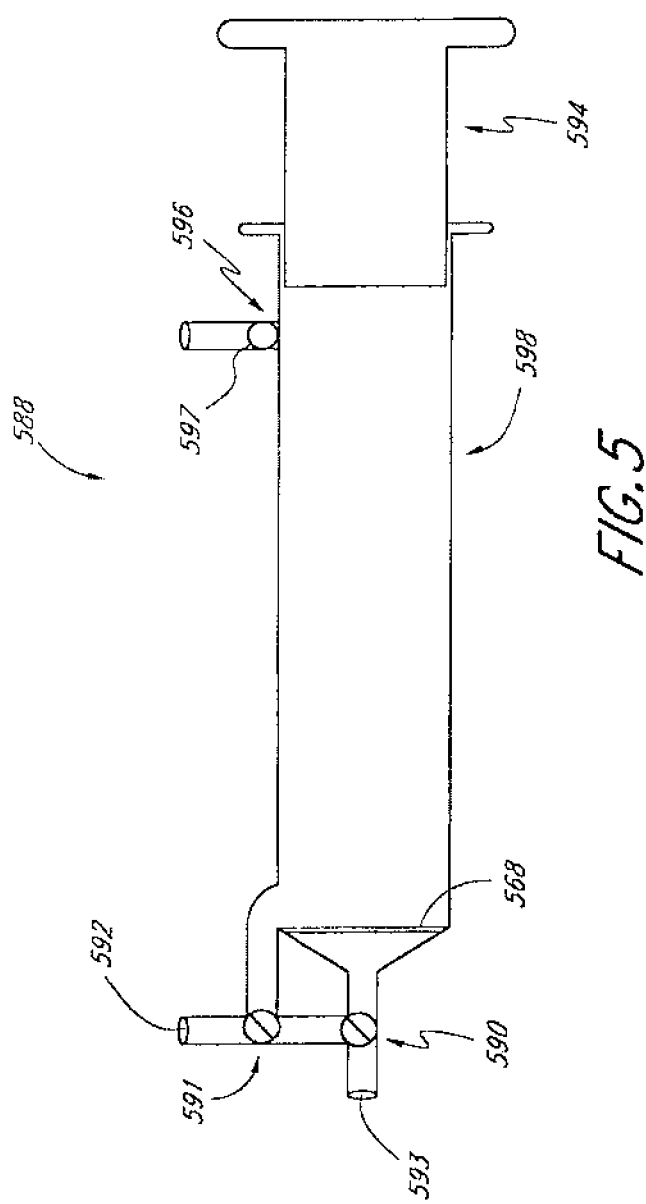

METHOD AND APPARATUS FOR TREATING A CAROTID ARTERY

RELATED APPLICATIONS

This application is a continuation of co-pending U.S. patent application Ser. No. 14/508,354, titled "Method And Apparatus For Treating A Carotid Artery," filed Oct. 7, 2014; which in turn is a continuation of U.S. patent application Ser. No. 12/966,974, titled "Method And Apparatus For Treating A Carotid Artery," filed Dec. 13, 2010, now U.S. Pat. No. 8,870,805; which in turn is a continuation of U.S. patent application Ser. No. 10/996,301, titled "Method And Apparatus For Treating A Carotid Artery," filed Nov. 22, 2004, now U.S. Pat. No. 7,998,104; which claims the benefit under 35 U.S.C. §119(e) of the following U.S. Provisional Applications: (1) U.S. Provisional Patent Application Ser. No. 60/524,069, filed Nov. 21, 2003, titled "Method And Apparatus For Carotid Angioplasty And Stenting Using Transcervical Occlusion And Protective Shunting;" (2) U.S. Provisional Patent Application Ser. No. 60/569,843, filed May 10, 2004, titled "Method And Apparatus For Carotid Angioplasty And Stenting Using Transcervical Occlusion And Protective Shunting;" and (3) U.S. Provisional Patent Application Ser. No. 60/587,067, filed Jul. 12, 2004, titled "Method And Apparatus For Carotid Angioplasty And Stenting Using Transcervical Occlusion And Protective Shunting." Priority of the aforementioned filing dates is hereby claimed, and the disclosures of the Applications are hereby incorporated by reference in their entirety.

BACKGROUND OF THE INVENTION

Field of the Invention

Certain inventions disclosed herein relate to treating a carotid artery. For example, a carotid artery may have a lesion or a partial occlusion that can be treated using the methods and apparatus disclosed herein.

Description of the Related Art

Carotid angioplasty and stenting (CAS) is a minimally invasive approach for treating carotid stenoses. Since its introduction two decades ago, the use of CAS has steadily increased, with 8% of the 107,000 carotid procedures performed in Europe in 2001 utilizing CAS. The prospect of an outpatient procedure without the discomfort of a sizable neck incision appears to be driving patient decision making away from carotid endarterectomy, the standard procedure for carotid bifurcation disease for the past fifty years.

SUMMARY OF THE INVENTION

One disclosed embodiment comprises an apparatus for use in carotid angioplasty. The apparatus comprises a catheter having a distal end and a proximal end opposite the distal end, and first and second occlusive members, of which at least the first occlusive member is located on the catheter. The first and second occlusive members are configured to reverse the natural direction of blood flow in the internal carotid artery when the first occlusive member occludes the common carotid artery and the second occlusive member occludes the external carotid artery. The catheter has a first shaft portion extending proximally from the first occlusive member. The first shaft portion has a maximum cross-section sized to be insertable into the common carotid artery. The first shaft portion has a relatively short length suitable for transcervical access to the common carotid artery. The catheter has a blood entry port located distal of the first occlusive member. The apparatus further comprises a collection reservoir configured to be connected to the catheter and placed in passive fluid communication with the blood entry port.

Another disclosed embodiment comprises a method of treating a lesion in a carotid artery in a patient. The method comprises inserting a catheter into the carotid vasculature via a transcervical approach, and occluding blood flow in the common carotid artery and the external carotid artery, thus reversing the direction of natural blood flow in the internal carotid artery. The method further comprises allowing blood to flow into a blood entry port in the catheter, and passively collecting the blood in a reservoir.

Another disclosed embodiment comprises an apparatus for use in carotid angioplasty. The apparatus comprises a catheter having a distal end and a proximal end opposite the distal end, and first and second occlusive members, of which at least the first occlusive member is located on the catheter. The first and second occlusive members are configured to reverse the natural direction of blood flow in the internal carotid artery when the first occlusive member occludes the common carotid artery and the second occlusive member occludes the external carotid artery. The catheter has a first shaft portion extending proximally from the first occlusive member. The first shaft portion has a maximum cross-section sized to be insertable into the common carotid artery. The first shaft portion has a relatively short length suitable for transcervical access to the common carotid artery. The catheter has a blood entry port located distal of the first occlusive member. The apparatus further comprises a passive fluid conduit and a collection reservoir. The collection reservoir is configured to be connected to the catheter via the passive fluid conduit.

Another disclosed embodiment comprises a method for treating lesions in the carotid artery of a mammalian body. The method comprises transcervical access and blocking of blood flow through the common carotid artery, shunting blood from the internal carotid artery to the venous system of the mammalian body and treating the lesion in the carotid artery. The method may optionally further comprise blocking blood flow through the external carotid artery.

In the method, access to the carotid artery can optionally be obtained percutaneously, or via a cutdown incision, or with any suitable technique. The treating step of the method can optionally include dilating the lesion with a balloon. The treating step of the method can optionally include stenting the dilated lesion. The shunting step of the method can optionally include filtering the blood for debris. The blocking step of the method can optionally include occluding the external carotid artery with a balloon. The blocking step of the method can optionally include occluding the common carotid artery with a balloon. The blocking step of the method can optionally include clamping the common carotid artery. The introducing step of the method can optionally include positioning a single sheath with balloons to occlude the common and external carotid artery and a side port for deployment of an angioplasty balloon or stent. The blocking step of the method can optionally include introducing at least one catheter directly into the common carotid artery. The introducing step of the method can optionally include introducing first and second introducer sheaths directly into the common carotid artery. The introducing step of the method can optionally include introducing first and second balloon catheters directly into the common carotid artery.

Another disclosed embodiment comprises a method for treating lesions in the carotid artery. The method comprises transcervical access, blocking blood flow through the common carotid artery to allow safe treatment of the lesion and returning blood flow back to the carotid artery. The method may further comprise blocking blood flow through the external carotid artery.

In the method, the blood in the carotid artery may be actively withdrawn and returned to the carotid artery. In the method, access to the carotid artery can optionally be obtained percutaneously, or via a cutdown incision, or with any suitable technique. The treating step of the method can optionally include dilating the lesion with a balloon. The treating step of the method can optionally include stenting the dilated lesion. The shunting step of the method can optionally include filtering the blood for debris. The blocking step of the method can optionally include occluding the external carotid artery with a balloon. The blocking step of the method can optionally include occluding the common carotid artery with a balloon. The blocking step of the method can optionally include clamping the common carotid artery. The introducing step of the method can optionally include positioning a single sheath with balloons to occlude the common and external carotid artery and a side port for deployment of an angioplasty balloon or stent. The blocking step of the method can optionally include introducing at least one catheter directly into the common carotid artery. The introducing step of the method can optionally include introducing first and second introducer sheaths directly into the common carotid artery. The introducing step of the method can optionally include introducing first and second balloon catheters directly into the common carotid artery.

Another disclosed embodiment comprises a method for treatment of lesions in the carotid artery. The method comprises transcervical access, blocking blood flow through the common carotid artery and passive collection of blood and debris and subsequent return of filtered blood to the carotid artery. The method may further comprise blocking blood flow through the external carotid artery.

In the method, access to the carotid artery can optionally be obtained percutaneously, or via a cutdown incision, or with any suitable technique. The treating step of the method can optionally include dilating the lesion with a balloon. The treating step of the method can optionally include stenting the dilated lesion. The shunting step of the method can optionally include filtering the blood for debris. The blocking step of the method can optionally include occluding the external carotid artery with a balloon. The blocking step of the method can optionally include occluding the common carotid artery with a balloon. The blocking step of the method can optionally include clamping the common carotid artery. The introducing step of the method can optionally include positioning a single sheath with balloons to occlude the common and external carotid artery and a side port for deployment of an angioplasty balloon or stent. The blocking step of the method can optionally include introducing at least one catheter directly into the common carotid artery. The introducing step of the method can optionally include introducing first and second introducer sheaths directly into the common carotid artery. The introducing step of the method can optionally include introducing first and second balloon catheters directly into the common carotid artery.

Certain objects and advantages of the invention are described herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of the embodiments summarized above are intended to be within the scope of the invention herein disclosed. However, despite the foregoing discussion of certain embodiments, only the appended claims (and not the present summary) are intended to define the invention. The summarized embodiments, and other embodiments of the present invention, will become readily apparent to those skilled in the art from the following detailed description of the preferred embodiments having reference to the attached figures, the invention not being limited to any particular embodiment(s) disclosed.

BRIEF DESCRIPTION OF THE DRAWINGS

FIG. 3A is a side view of a blocker and pusher rod usable with apparatus and methods disclosed herein, including the apparatus and methods of FIG. 3.

FIG. 3B is a detail view of another embodiment of the catheter shown in FIG. 3.

FIG. 5 is a schematic view of another embodiment of the pump reservoir of FIG. 4.

DETAILED DESCRIPTION OF THE PREFERRED EMBODIMENT

An approach called Transcervical Occlusion (of the CCA) and Proximal Shunting (TOPS) can be employed in carotid angioplasty.

Figure 1:
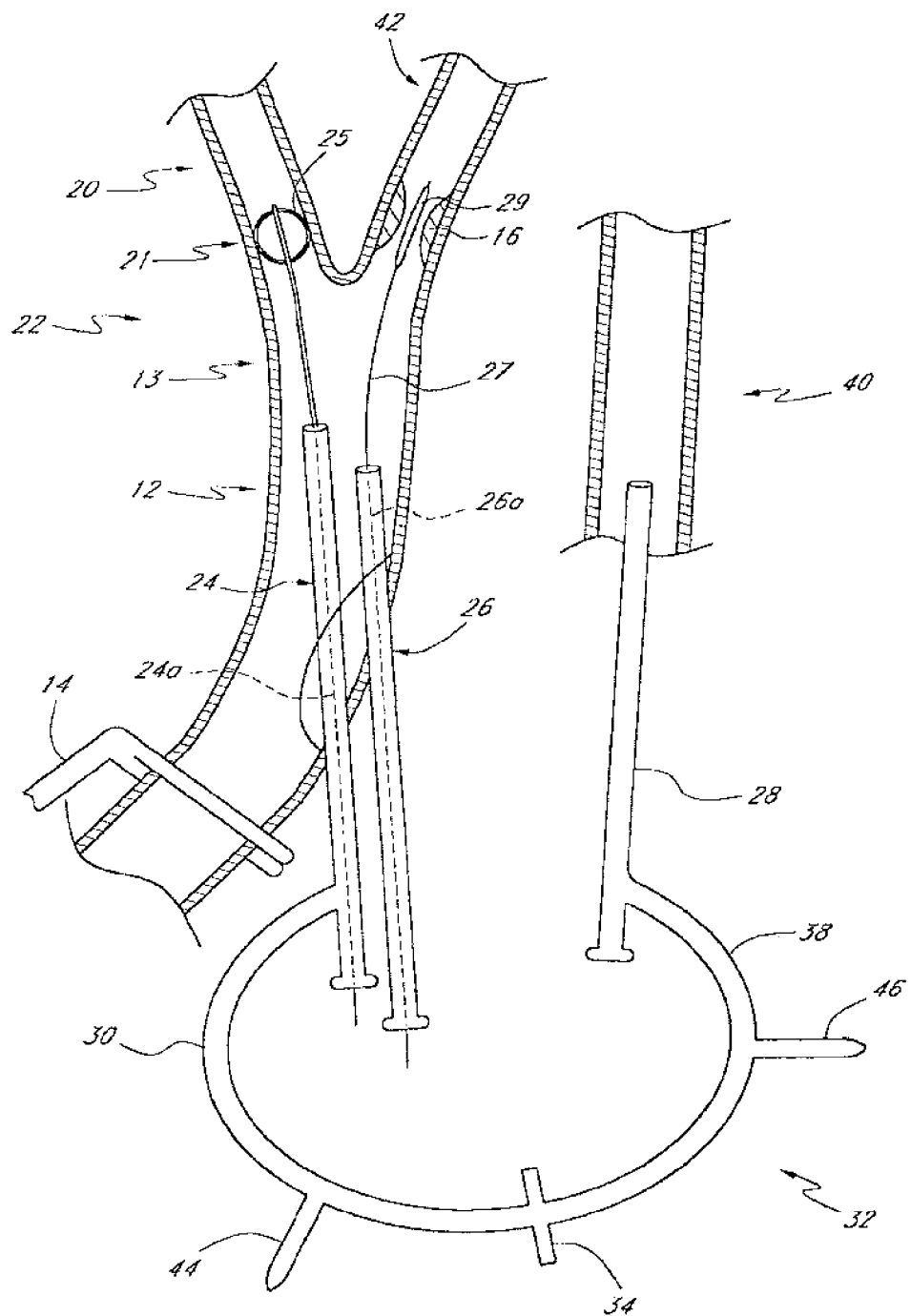
FIG. 1 is a schematic view of one embodiment of a method and apparatus for treating a carotid artery.

In one embodiment, depicted in FIG. 1, a method of treating a carotid artery can be performed in the operating theater. After mild sedation of the patient, a mixture of 1% lidocaine and 0.5% marcaine can be used to anesthetize the skin two centimeters above the clavicle. A 2 cm transverse incision is made centered over the medial border of the sternocleidomastoid muscle. The muscle is retracted laterally and the common carotid artery (CCA) 12 exposed circumferentially over a two-centimeter length.

After heparin (for example, about 70 IU/kg to about 100 IU/kg) is administered to increase the activated clotting time (to greater than 250 seconds, for example), a needle (not shown) is introduced directly into the CCA 12 above the position of a surgical clamp 14. Injection of contrast under fluoroscopy in the appropriate anterior oblique plane localizes the carotid bifurcation and the lesion 16 in a "worst view" magnified angiogram. A guidewire (not shown) is advanced to the distal carotid bulb 22 or to the external carotid artery 20. A first sheath 24 is advanced until the dilator (a component of the sheath not shown) straightens the tip of the guidewire and then the sheath 24 is advanced over the dilator to the distal CCA 13 or the external carotid artery (ECA) 20. Intracranial carotid angiography is performed (AP Towne and lateral view) to document any pre-existent intracranial arterial pathology and to evaluate collateral circulation.

The first sheath 24 can be placed directly in the CCA 12 parallel to a smaller second introducer sheath 26 placed with its tip in the distal CCA 13. A stitch may be placed around the entrance of the first sheath 24 and a vascular tourniquet (not shown) and umbilical tape (not shown) may be looped around the CCA to allow rapid hemostasis of the puncture site in the event of catheter dislodgement. A guidewire is directed into the ECA 20 through the first arterial sheath 24 and a balloon catheter 25 is used to occlude the proximal ECA 21. Occlusion of the ECA 20 and reversal of blood flow in the internal carotid artery (ICA) 42 can be verified with angiography after clamping the CCA 12.

A sidearm 30 of the first sheath 24 is connected to a filter 34 with a holder apparatus (not shown) that is attached to a sidearm 38 of a third sheath 28 in fluid communication with the internal jugular vein 40. This configuration forms a shunt 32. With the surgical clamp 14 applied to the CCA 12, retrograde flow of contrast from the internal carotid artery (ICA) 42 into the internal jugular vein 40 through the shunt 32 can be confirmed using fluoroscopy or duplex ultrasound. The carotid lesion 16 is crossed with a guidewire 27 from the second sheath 26 under flow reversal cerebral protection and the lesion 16 is dilated with a balloon 29.

If rapid retrograde flow of contrast is not seen with initiation of the shunt 32, forceful aspiration of blood using a syringe (for example a 20 cc syringe) through the first sheath 24 is performed, for example, after each angioplasty. Hence, retrograde passage of embolic material is provided. The blood is returned to the patient through a three way stopcock (for example, stopcock 44 and stopcock 46) attached to the shunt 32 or filter 34. A stent (for example an 8 or 10 mm×24 mm stent) can be deployed across the lesion 16 into the CCA 12. The stent can be serially post dilated with an angioplasty balloon (for example a 5 or 6 mm×2 cm angioplasty balloon).

Completion of cervical and intracranial carotid angiography is performed after releasing the external carotid occlusion balloon 25 and the common carotid clamp 14. Once satisfactory treatment of the lesion 16 is observed, the first arterial sheath 24 and second arterial sheath 26 are removed with simultaneous repair of the arterial punctures using previously placed exit site sutures.

In some embodiments, either or both of the sheaths 24, 26 may have an insertable length or first shaft portion extending proximally from the distal end of the sheath(s). Over the entirety of the insertable length, the sheath(s) 24, 26 have a cross-sectional size (e.g., about 6-8 French) which is suitable for insertion into the CCA 12. (Although the cross-sectional size need not be uniform along the insertable length, the maximum cross-sectional size along the insertable length should be suitable for insertion into the CCA.) In certain such embodiments, the insertable length is less than about 75 cm, less than about 50 cm, less than about 30 cm, or less than about 15 cm. In still other embodiments, the insertable length is between about 2 cm and about 25 cm, or between about 2 cm and about 15 cm. More generally, the insertable length may be relatively short as may be suitable for transcervical access to the CCA.

In some embodiments, one or both of the shafts 24a, 26a of the sheaths 24, 26 is constructed to be generally rigid. Advantageously, a rigid sheath 24/26 can be inserted into the CCA 12 without need to "ride" the sheath 24/26 over a guidewire. As another alternative either shaft 24a/26a may be made generally rigid but sufficiently malleable to permit the user to "pre-bend" the shaft 24a/26a, such that the shaft maintains the bent shape imparted by the user. With such a malleable shaft 24a/26a, the user can custom-shape the sheath 24/26 to fit the vasculature of the patient, and more easily manipulate the sheath 24/26 into position in the CCA 12. The pre-bend may be made based on the user's observations of the patient's carotid vasculature. A sheath 24/26 which is rigid and/or malleable as discussed above can be made from stainless steel or suitable soft metals, or any suitable polymeric materials.

Figures 2, 2A:
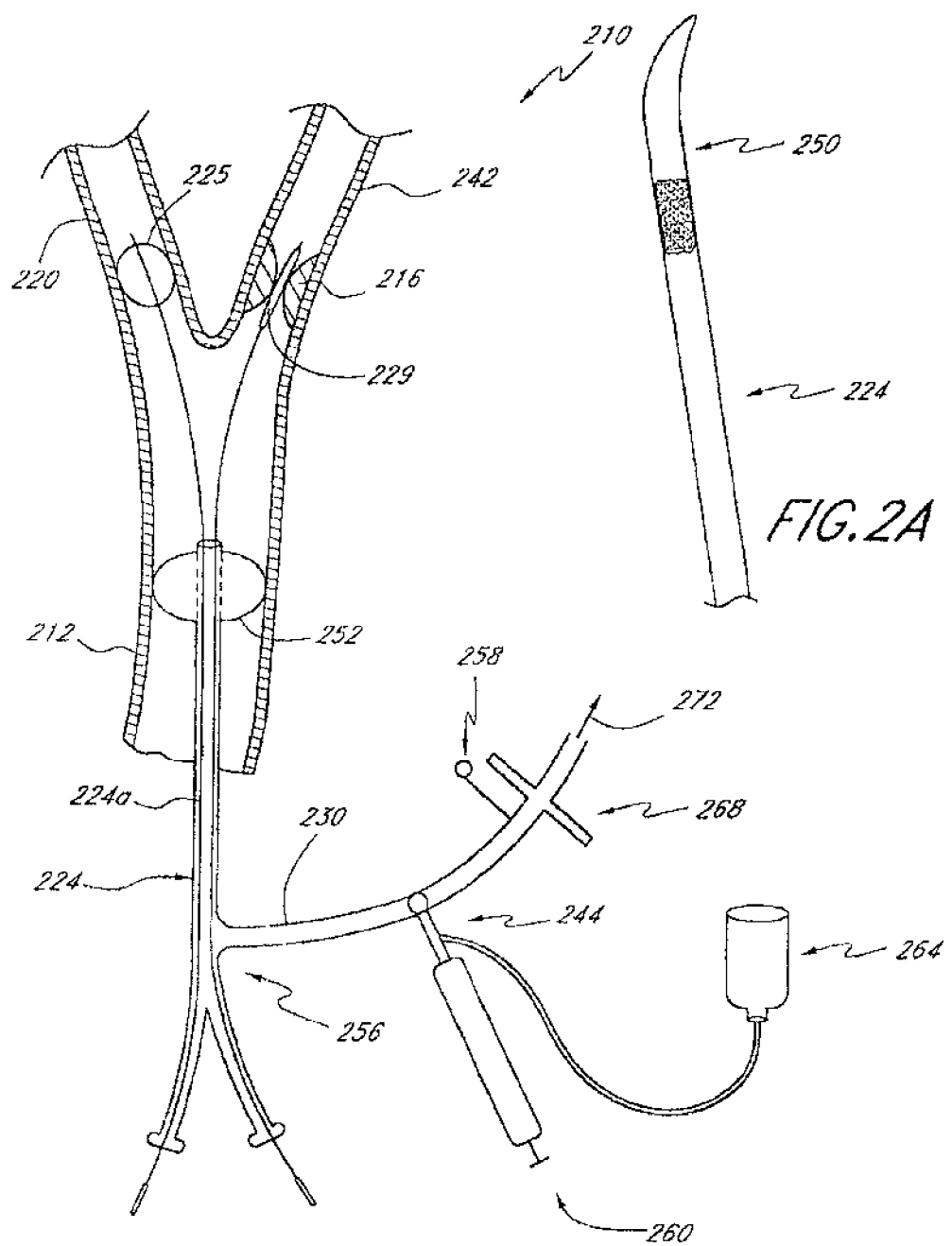
FIG. 2 is a schematic view of another embodiment of a method and apparatus for treating a carotid artery.
FIG. 2A is a side view of a dilator tip usable with apparatus and methods disclosed herein, including the apparatus and methods of FIG. 2.

In another embodiment, illustrated in FIGS. 2 and 2A, a device 210 with only one arterial sheath or catheter 224 is used. A dilator 250 (see FIG. 2A) for the arterial sheath 224 may have a shorter taper than conventional arterial sheaths and may be angled or curved towards the tip to help prevent injury to or dissection of the back wall of the artery. The stent/ICA angioplasty balloon 229 and the ECA occlusion balloon 225 are passed through the single sheath 224, which is preferably large enough to deploy both balloons 225, 229 as well as provide a lumen of sufficient size to facilitate retrograde passage of embolic material through the sheath 224. This sheath may have a balloon 252 that prevents the sheath from dislodging and also may be large enough to occlude the CCA 212, effectively replacing the surgical clamp 14 of the embodiment of FIG. 1. The lesion 216 in the ICA 242 may be crossed with a guidewire and dilated with the stent/ICA angioplasty balloon 229. The sidearm 230 of the arterial sheath 224 may have an opening 256, which is preferably larger than the opening of a typical sheath, thus preventing a bottleneck for flow of blood carrying large embolic debris. A flow sensor 258 (a Doppler sensor, for example) may be part of the flow circuit, allowing for real-time and failsafe verification of flow and direction. A contrast injection/blood aspiration apparatus 260 can be attached to the sidearm 230 near the sideport 256, along with a contrast reservoir 264, to prevent inadvertent air embolism. A stopcock 244 can be employed at the junction between the sidearm 230 and injection/aspiration apparatus 260. When stopcock 244 is open, the opened passage preferably has a large lumen. A filter 268 can also be attached to the sidearm 230. The filter apparatus may be made integral to the device 210 to simplify the components in the device 210. As indicated by flow arrow 272, sidearm 230 can lead to a venous sheath (not shown) such as the sheath 28 of the embodiment of FIG. 1.

In some embodiments, the sheath 224 may have an insertable length or first shaft portion extending proximally from the balloon 252. Over the entirety of the insertable length, the sheath 224 has a cross-sectional size (e.g., about 6-8 French) which is suitable for insertion into the CCA 12. (Although the cross-sectional size need not be uniform along the insertable length, the maximum cross-sectional size along the insertable length should be suitable for insertion into the CCA.) In certain such embodiments, the insertable length is less than about 75 cm, less than about 50 cm, less than about 30 cm, or less than about 15 cm. In still other embodiments, the insertable length is between about 2 cm and about 25 cm, or between about 2 cm and about 15 cm. More generally, the insertable length may be relatively short as may be suitable for transcervical access to the CCA.

In some embodiments, the shaft 224a of the sheath 224 is constructed to be generally rigid. Advantageously, a rigid sheath 224 can be inserted into the CCA 12 without need to "ride" the sheath 224 over a guidewire. As another alternative the shaft 224a may be made generally rigid but sufficiently malleable to permit the user to "pre-bend" the shaft 224a, such that the shaft maintains the bent shape imparted by the user. With such a malleable shaft 224a, the user can custom-shape the sheath 224 to fit the vasculature of the patient, and more easily manipulate the sheath 224 into position in the CCA 12. The pre-bend may be made based on the user's observations of the patient's carotid vasculature. A sheath 224 which is rigid and/or malleable as discussed above can be made from stainless steel or suitable soft metals, or any suitable polymeric materials.

Figure 3:
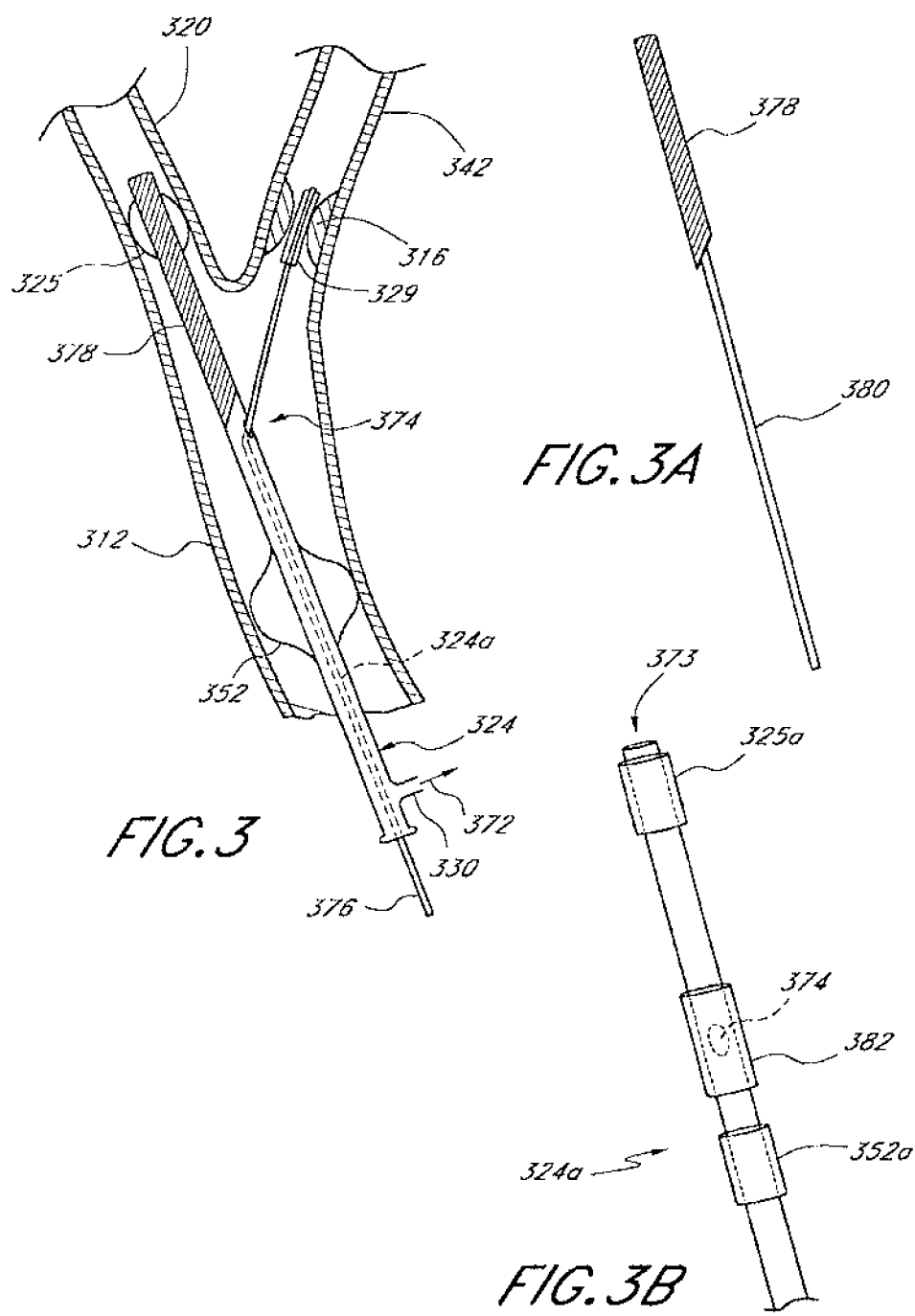
FIG. 3 is a schematic view of another embodiment of a method and apparatus for treating a carotid artery.

In a further embodiment, illustrated in FIGS. 3, 3A and 3B, the arterial catheter/sheath 324 of the apparatus has an opening 374 in the side of the sheath distal of a first inflatable membrane or balloon 352, located on the outside of the sheath 324. A second inflatable membrane or balloon 325 is located on the outside of the sheath 324, distal of the opening 374. The balloon sheath 324 is inserted into the ECA 320, for example over a guidewire (not shown). After the guidewire (not shown) has been removed from the sheath 324, a blocker 378 (also shown in FIG. 3A) is passed through the sheath 324 to occlude the distal lumen 373 of the sheath 324. The blocker 378 can be delivered by means of a detachable pusher rod 380. Alternately, a valve (not shown) or other mechanism may be fashioned to close the lumen 373 of the sheath 324 leading to ECA 320 after removal of the guidewire. The second balloon 325 is then inflated to create a seal preventing flow in the ECA 320. The first balloon 352 may be inflated to occlude the CCA 312. An angioplasty balloon and stent 329 may then be passed over a guidewire 376 through the side opening 374 in the arterial sheath 324, and into the internal carotid artery 342, with or without predilation angioplasty of the lesion 316.

In one embodiment, the first balloon 352 has an inflated diameter of up to about 13 mm and the second balloon 325 has an inflated diameter of up to 6 mm. The balloons are preferably spaced about 2-6 cm apart on the sheath 324.

A sliding or removable sleeve 382 (see FIG. 3B) may be included to cover the side opening 374 in the arterial sheath 324, allowing two catheters (not shown) to pass through the sheath 324 without blood leakage out of the sheath 324 into the operative field external of the patient. The flexible and removable sleeve 382 may be formed from any suitable material such as plastic or be formed from any suitable peelable tape.

A sheath equipped with the sleeve 382 may be useful, for example, for treating common carotid lesions (not shown) or treating internal carotid lesions when the ECA is occluded. In these cases, the sheath cannot be extended into the occluded ECA so only the very tip of the sheath 324 with the distal second balloon 325 is placed into and occludes the CCA 352. There is no need for a separate ECA occlusion balloon if the ECA is already occluded or severely narrowed with disease. Such a positioning of the sheath may result in the side opening 374 or hole in the sheath being external the patient. The side opening 374 is thus covered with the sleeve 382 to inhibit or prevent blood from spurting out of the sheath 324 onto the operative field.

An occluded ECA is not shown in FIG. 3, but the following description assumes an occluded ECA, and the second balloon 325 positioned in, and occluding, the CCA 312. A catheter (e.g. the catheter 329) for performing angioplasty and stent deployment is passed through the end of the sheath for positioning in the ICA 342. In this manner, the sheath 324 of FIG. 3 operates in a manner similar to the sheath 224 of FIG. 2, with the second balloon 325 serving to occlude the CCA 312. The first uninflated balloon 352 of the sheath 324 remains outside of the patient and thus inactive. Note, in this case, no blocker 378 is used.

If the ECA is not occluded, the sleeve 382 can be either peeled away or slid away to allow the sheath 324 to be pushed farther distally through the incision and into the hole in the artery so that the second balloon 325 is positioned in the ECA 320. Such a placement of the sheath 324, as discussed above, permits deployment of the stent 329 through the sidehole 374 instead of through the end hole 373 of the sheath 324. The decision concerning where to place the tip of the sheath is made during the initial angiogram. As can be appreciated, such a sheath may also be useful for performing the procedure illustrated in FIG. 2.

As indicated by flow arrow 372, a sidearm 330 of the sheath 324 can lead to a shunt such as the shunt 32 described above, a filter, a contrast injection/blood aspiration apparatus such as the apparatus 260 described above, a contrast reservoir such as the reservoir 264 described above, stopcocks, a venous sheath such as the sheath 28 of FIG. 1, or any combination of the above.

Figures 4, 4A:
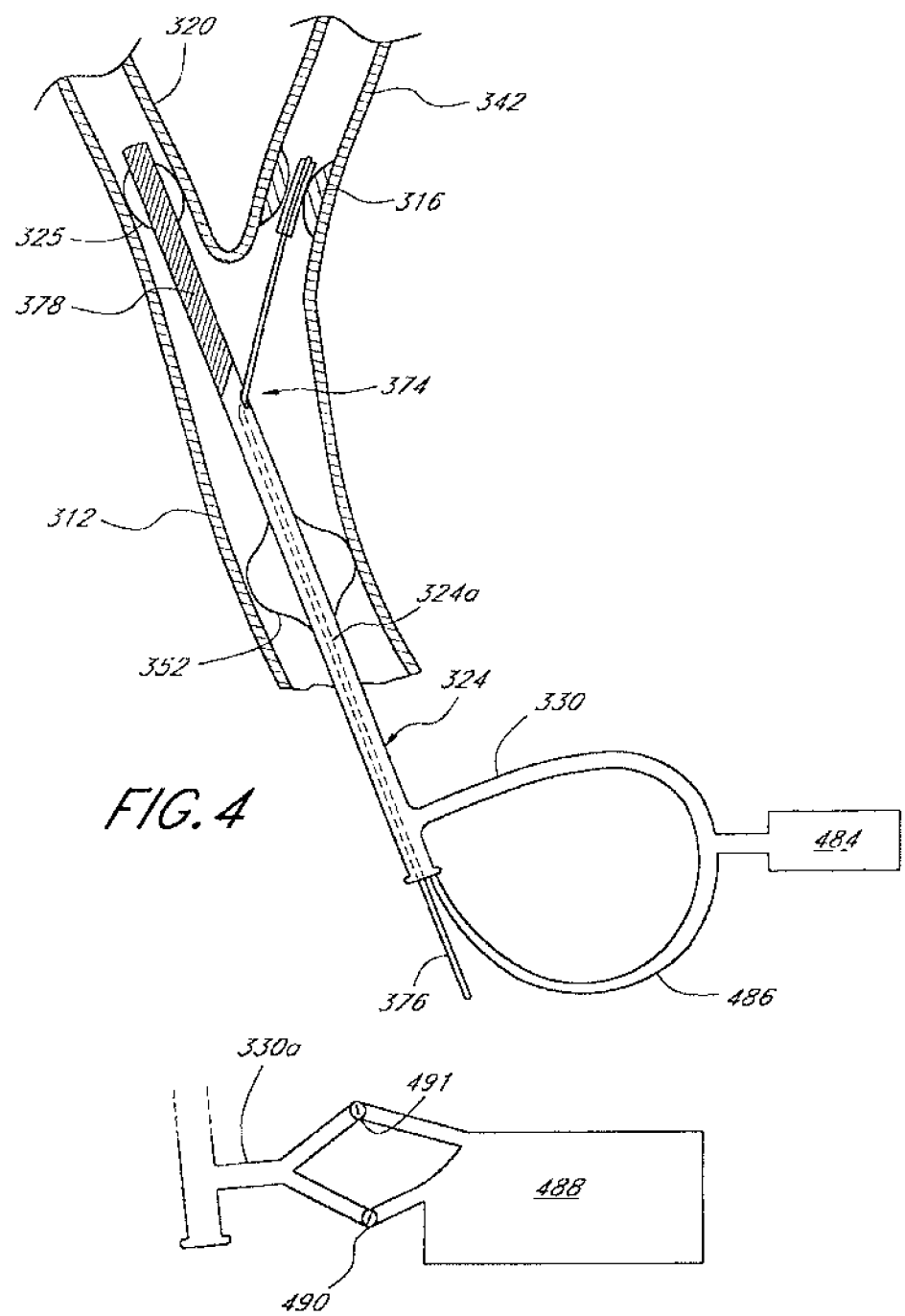
FIG. 4 is a schematic view of another embodiment of a method and apparatus for treating a carotid artery.
FIG. 4A a schematic view of another embodiment of the pump reservoir shown in FIG. 4.

In an alternative embodiment, the sheath 324 of FIGS. 3-4 may have a closed distal tip (instead of the open tip and blocker shown in FIGS. 3-4). Such a closed distal tip preferably has a tapered, atraumatic configuration. With a closed distal tip, the sheath 324 can be inserted into the CCA 12 and ECA 320 without the use of a guidewire.

In some embodiments, the sheath 324 may have an insertable length or first shaft portion extending proximally from the first balloon 352. Over the entirety of the insertable length, the sheath 324 has a cross-sectional size (e.g., about 6-8 French) which is suitable for insertion into the CCA 12. (Although the cross-sectional size need not be uniform along the insertable length, the maximum cross-sectional size along the insertable length should be suitable for insertion into the CCA.) In certain such embodiments, the insertable length is less than about 75 cm, less than about 50 cm, less than about 30 cm, or less than about 15 cm. In still other embodiments, the insertable length is between about 2 cm and about 25 cm, or between about 2 cm and about 15 cm. More generally, the insertable length may be relatively short as may be suitable for transcervical access to the CCA.

In some embodiments, the shaft 324a of the sheath 324 is constructed to be generally rigid. Advantageously, a rigid sheath 324 can be inserted into the CCA 12 without need to "ride" the sheath 324 over a guidewire. As another alternative the shaft 324a may be made generally rigid but sufficiently malleable to permit the user to "pre-bend" the shaft 324a, such that the shaft maintains the bent shape imparted by the user. With such a malleable shaft 324a, the user can custom-shape the sheath 324 to fit the vasculature of the patient, and more easily manipulate the sheath 324 into position in the CCA 12. The pre-bend may be made based on the user's observations of the patient's carotid vasculature. A sheath 324 which is rigid and/or malleable as discussed above can be made from stainless steel or suitable soft metals, or any suitable polymeric materials.

Certain embodiments do not employ venous shunting. One such embodiment is illustrated in FIG. 4. The arterial sheath sidearm 330 is in fluid communication with a pump 484 that allows control and verification of the amount of flow. After passing through a filter (that can be included with pump 484), the blood is returned to the arterial sheath 324. Blood return may be accomplished through a separate arterial channel 486 or by causing the blood to flow into a pump reservoir 488 (see FIG. 4A) and returning the blood through the same sidearm port 330a after the period of cerebral protection. The latter approach may employ valves such as valves 490 and 491.

FIG. 5 illustrates an embodiment of a reservoir apparatus 588 that may be employed to passively collect blood from the sidearm 30/230/330 of the sheath 24/224/324. The apparatus 588 comprises a filter 568, valves 590, 591 and 597, blood inlet port 592, blood outlet port 593, plunger 594, reservoir 598, and air outlet port 596. The sidearm 30/230/330 is connected to the blood inlet port 592 and the valve 591 is initially set to permit blood flowing from the sidearm to flow from the inlet port 592 into the reservoir 598, while the valve 590 is initially set to prevent fluid from flowing from the reservoir 598 past the valve 590. In addition, the blood outlet port is connected to an arterial or venous return line, e.g. the arterial channel 486. During the period of cerebral protection (when the arterial blood flow is reversed via the balloon(s) and/or clamp disclosed above), this initial setup permits arterial blood to flow "passively" under natural arterial pressure, proximally through the sheath 24/224/324, through the sidearm 30/230/330 and into the reservoir 598, without need for additional or external pressure sources. Thus the arterial blood is collected passively in the reservoir apparatus 588; as the blood is collected in the reservoir 598 air is vented through the air outlet port 596 (the valve 597 of which is left open for this purpose).

After the period of cerebral protection is over and the natural direction of blood flow is restored (e.g., via deflation of the balloon(s) and/or release of the clamp), the collected blood can be returned to the patient's vasculature, e.g. via the CCA 12 and implanted sheath 24/224/324. To do this the valves 591 and 597 are closed, and the valve 590 is opened. The plunger 594 is then depressed to force the collected blood out of the reservoir 598, through the filter 568 and valve 590, and out through the blood outlet port 593. If a return line such as the arterial channel 486 is employed, the blood proceeds through the channel 486 and implanted sheath, and back into the CCA 12.

If desired a non-rigid overflow chamber (such as a ventilated bag) can be connected to the air outlet port 596 to collect any blood that overflows the reservoir 598. As yet another option, a metering valve (not shown) can be installed on the sidearm 30/230/330 (or between the sidearm and the reservoir 598) to adjust the blood flow rate into the reservoir 598, to account for patient-to-patient variation in natural arterial flow rates.

As a further option, a contrast reservoir (not shown) can be coupled to the return line/arterial channel downstream of the blood outlet port 593, via a "T" fitting or the like, to add contrast fluid as desired to the blood as it returns to the patient.

Additional embodiments comprise kits. A first kit comprises the apparatus of FIG. 1; a second kit comprises the apparatus of FIGS. 2-2A; a third kit comprises the apparatus of FIGS. 3-3B; a fourth kit comprises the apparatus of FIG. 4; a fifth kit comprises the apparatus of FIG. 4, with the apparatus of FIG. 4A substituted for the corresponding apparatus of FIG. 4. A sixth kit comprises the apparatus of FIG. 4, with the apparatus of FIG. 5 substituted for the corresponding apparatus of FIG. 4. Any of the aforementioned kits may further comprise special short-length (e.g. 15-45 cm) guidewires appropriate to the cervical approach. These short-length guidewires may be constructed to be malleable and retain a bent shape imparted by the user, in a manner similar to the malleable sheaths discussed above. Such guidewires can be constructed from stainless steel or suitable soft metals, and can be made thicker than typical guidewires.

Instead of or in addition to these short-length guidewires, any of the kits mentioned above may comprise a "bent" introducer needle with appropriate angulation to decrease the likelihood of backwall arterial puncture. The introducer needle may have a contrast injection sideport.

Although these inventions have been disclosed in the context of certain preferred embodiments and examples, it will be understood by those skilled in the art that the present invention extends beyond the specifically-disclosed embodiments to other alternative embodiments and/or uses of the inventions and obvious modifications and equivalents thereof. In addition, while a number of variations of the inventions have been shown and described in varying levels of detail, other modifications, which are within the scope of this invention, will be readily apparent to those of skill in the art based upon this disclosure. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present invention herein disclosed should not be limited by the particular disclosed embodiments described above, but should be determined only by a fair reading of the claims that follow.

What is claimed is:

1. A method of treating a carotid artery, comprising:
   forming a puncture opening through a wall of the common carotid artery;
   positioning through the puncture an arterial access sheath and dilator system, the positioning comprising inserting the arterial access sheath and dilator system through the puncture without previously inserting an introducer device through the puncture, wherein the arterial access sheath and dilator system comprises an arterial access sheath and a dilator inside the arterial access sheath, wherein the arterial access sheath comprises a first occlusion element adapted to occlude the carotid artery and wherein the dilator comprises a tapered distal end; and
   removing the dilator from the arterial access sheath; and
   expanding the first occlusion element to occlude the carotid artery.

2. A method as in claim 1, wherein forming the puncture opening comprises making the puncture opening directly into the common carotid artery accessed through a transcervical surgical incision.

3. A method as in claim 1, wherein forming the puncture opening comprises performing a percutaneous puncture into the common carotid artery.

4. A method as in claim 1, further comprising:
   reversing the direction of natural blood flow in the carotid artery; and
   shunting blood from the carotid artery to a venous system of the patient via the arterial access sheath.

5. A method as in claim 1, further comprising:
   introducing a therapeutic catheter through the arterial access sheath; and
   treating the carotid artery.

6. A method as in claim 5, wherein the therapeutic catheter is a stent delivery catheter and treating the carotid artery comprises deploying a stent using the stent delivery catheter.

7. A method as in claim 1, wherein the arterial access sheath comprises a second occlusion element distal of the first occlusion element, and further comprising:

positioning the second occlusion element in an external carotid artery branching from the common carotid artery; and expanding the second occlusion element to occlude the external carotid artery.

8. A method as in claim 7, further comprising:

introducing a therapeutic catheter into the carotid artery through an exit port located on the side of the arterial access sheath between the first and second occlusion elements; and treating the carotid artery.

9. A method as in claim 1, wherein the first occlusion element is an inflatable balloon.

10. A method as in claim 1, wherein the dilator comprises an internal lumen configured to receive a guidewire.

11. A method as in claim 1, wherein forming the puncture comprises forming the puncture with a needle, and wherein positioning through the puncture an arterial access sheath and dilator system comprises inserting a guidewire through the needle, removing the needle, and advancing the arterial access sheath system over the guidewire.

12. A method of treating a carotid artery, comprising:

forming a puncture opening through a wall of the common carotid artery;

positioning through the puncture an arterial access sheath and dilator system, wherein the arterial access sheath and dilator system comprises an arterial access sheath and a dilator inside the arterial access sheath, wherein the arterial access sheath comprises a first occlusion element adapted to occlude the carotid artery and a second occlusion element distal of the first occlusion element, and wherein the dilator comprises a tapered distal end;

removing the dilator from the arterial access sheath;

expanding the first occlusion element to occlude the carotid artery;

positioning the second occlusion element in an external carotid artery branching from the common carotid artery;

expanding the second occlusion element to occlude the external carotid artery;

introducing a therapeutic catheter into the carotid artery through an exit port located on the side of the arterial access sheath between the first and second occlusion elements; and treating the carotid artery.

13. A method of treating a carotid artery, comprising:

forming a puncture opening through a wall of the common carotid artery;

positioning through the puncture an arterial access sheath and dilator system, wherein the arterial access sheath and dilator system comprises an arterial access sheath and a dilator inside the arterial access sheath, wherein the arterial access sheath comprises a first occlusion element adapted to occlude the carotid artery, and wherein the dilator comprises a tapered distal end and an internal lumen configured to receive a guidewire;

removing the dilator from the arterial access sheath; and expanding the first occlusion element to occlude the carotid artery.

14. A system for use in accessing and treating a carotid artery, the system comprising:

an arterial access sheath comprising a lumen extending between a proximal end and a distal end adapted to receive blood flow from a carotid artery, and a dilator positionable within the lumen of the arterial access sheath, the arterial access sheath and dilator adapted to be collectively introduced through a puncture in the common carotid artery;

a first occlusion element coupled to the arterial access sheath at a distal region of the arterial access sheath and adapted to expand and occlude the carotid artery;

a second occlusion element coupled to the arterial access sheath at a position distal of the first occlusion element, wherein the second occlusion element is configured to expand and occlude the external carotid artery while the first occlusion element occludes the carotid artery;

a shunt fluidly connected to the arterial access sheath, wherein the shunt provides a pathway for blood to flow from the arterial access device to a return site; and a side opening located on the side of the sheath between the two occlusion elements, the shunt fluidly connected to the arterial access sheath at an exit port of the arterial access sheath.

* * * * *